United States Patent [19]

Faust

[11] Patent Number: 4,902,482
[45] Date of Patent: Feb. 20, 1990

[54] DEVICE AND RECEPTACLE FOR INHIBITING CONTAMINATION FOR INFECTIONS WASTE

[76] Inventor: Paul A. Faust, 26 Grantwood, St. Louis, Mo. 63123

[21] Appl. No.: 78,862

[22] Filed: Jul. 28, 1987

[51] Int. Cl.$^4$ .................................. B65D 90/28
[52] U.S. Cl. ................... 422/121; 220/1 T; 220/87; 229/125.19; 229/125.26; 250/455.1; 422/5; 422/24; 422/292
[58] Field of Search .............. 220/1 T, 87; 422/5, 422/24, 292, 121; 250/215, 455.1; 250/215, 455.1; 229/125.26, 125.19

[56] References Cited

U.S. PATENT DOCUMENTS

| | | |
|---|---|---|
| 2,281,630 | 5/1942 | Southard .................... 220/87 |
| 2,434,238 | 1/1948 | Wolfson .................... 220/87 |
| 2,573,548 | 10/1951 | Cunningham ............ 422/292 X |
| 2,652,173 | 9/1953 | Farrell ..................... 220/87 |
| 2,833,456 | 5/1958 | Welshenbach ........ 229/125.26 X |
| 2,887,264 | 5/1959 | Fallert ................ 229/125.26 X |
| 3,008,604 | 11/1961 | Garner ..................... 220/87 |
| 3,831,514 | 8/1974 | Jernstrom ................. 422/5 X |
| 4,047,775 | 9/1977 | Wolbrink .................. 422/5 X |
| 4,534,489 | 8/1985 | Bartlett .................. 220/1 TX |
| 4,719,851 | 1/1988 | Chesnut .................... 422/5 X |

OTHER PUBLICATIONS

Block, *Disinfection, Sterilization, and Preservation*, 3rd Ed., Lea & Febiger (1983) pp. 566–573.

*Primary Examiner*—Barry S. Richman
*Assistant Examiner*—Jill Johnston
*Attorney, Agent, or Firm*—Senniger, Powers, Leavitt and Roedel

[57] ABSTRACT

The device for inhibiting contamination from an infectious waste receptacle may comprise a frame, a lid pivotally mounted on the frame, and a bactericidal light source on the underside of the lid to kill bacteria on the exposed surface of the accumulated waste in the receptacle and establish a substantially bacteria-free interface above the infectious waste. The device may further include a plenum having a vent in communication with the interior of the receptacle to maintain the interior of the receptacle at a lower pressure than the surrounding environment and to draw the air displaced from the receptacle away from the the depositor. Finally, the device may include means for applying a disinfectant and/or deodorant to the accumulated waste.

28 Claims, 4 Drawing Sheets

DEVICE AND RECEPTACLE FOR INHIBITING CONTAMINATION FOR INFECTIONS WASTE

BACKGROUND AND SUMMARY OF THE INVENTION

This invention relates to a method and a device for inhibiting contamination from infectious waste receptacles, particularly while waste is being deposited therein, and in particular to a method and device for establishing a substantially bacteria-free interface between the infectious waste and the surrounding environment.

Large amounts of infectious waste are created in laboratories, doctor's offices, hospitals, and other health care facilities, but little consideration is given to its disposal. Typically, infectious waste is temporarily stored in waste receptacles on site until it can be collected and disposed of. These infectious waste receptacles are usually just standard waste cans provided with a plastic bag liner. These infectious waste receptacles, which may be located throughout the laboratory or health care facility, are a prime source of contamination. Even when the infectious waste receptacle is provided with a lid, bacteria can escape to the surrounding environment. The threat of contamination is particularly great while waste is being deposited because the depositor is in close proximity to the receptacle, the lid, if there is one, is open, and the deposition of waste displaces contaminated air from the receptacle.

Collecting and disposing of the accumulated infectious waste is also a problem. The infectious waste is usually collected by unskilled workers who simply close the plastic bag liner, remove it, and replace it. In the simple act of closing the plastic bag liner, the contaminated air inside the liner is usually squeezed out to obtain sufficient room to close the liner, exposing the worker and the surrounding environment to contamination. Furthermore, the liners are usually not sealed, and the subsequent transportation and handling of the liner can cause the liner to expel more air, adding to the risk of contamination. Periodically workers may clean the receptacles which may have been contaminated by leakage from the liner. This is a hazardous task that exposes both the worker and the surrounding environment to an added risk of contamination.

It is among the objects of the present invention to provide a method for inhibiting contamination from an infectious waste receptacle. It is therefore among the objects of the present invention to contain the infectious waste by providing a lid for the infectious waste receptacle, and to kill bacteria on the exposed surface of the accumulated waste in the receptacle and establish a substantially bacteria-free interface above the infectious waste by exposing the interior of the receptacle to bactericidal light. It is an object of some embodiments of the method to retard the escape of bacteria by maintaining the pressure in the receptacle lower than the surrounding environment. It is also an object of some embodiments of the method to remove the potentially contaminated air displaced from the receptacle by the deposition of waste by drawing such air away from the person depositing waste in the receptacle. Finally it is an object of some embodiments of the present method to supplement the bactericidal action of the light source by applying a disinfectant and/or deodorant to the accumulated waste in the receptacle.

It is also among the objects of the present invention to provide a device for inhibiting contamination from an infectious waste receptacle. It is therefore among the objects of the present invention to provide a device having a lid for closing the infectious waste receptacle and a light source to kill bacteria on the exposed surface of the accumulated waste in the receptacle and establish a substantially bacteria-free interface above the infectious waste. It is a further object of this invention to provide a device that permits hands-free operation of the lid to prevent cross-contamination among the users of the device. It is also an object of some embodiments of this invention to provide a device including means for maintaining the interior of the receptacle at a lower pressure than the surrounding environment when the lid is closed, to retard the escape of contaminants from the receptable. It is also an object of some embodiments of this invention to provide a device having means for removing the potentially contaminated air displaced from the receptacle by the deposition of waste, and in particular means for drawing such air away from the person depositing waste in the receptacle. Finally it is an object of some embodiments of this invention to provide a device with means for applying a disinfectant and/or deodorant to the exposed surface of the accumulated waste in the receptacle as the lid is operated to supplement the bactericidal action of the light source.

It is also among the objects of the present invention to provide a receptacle for infectious waste that provides secure and leakproof containment of infectious waste; to provide such a receptacle that is at least partially rigid to prevent the receptacle from expelling contaminated air while being handled; to provide such a receptacle that is of inexpensive construction to be economically disposable; to provide such a device that is light weight, and preferably collapsable or stackable for compact storage and shipment.

Generally, the method of the present invention comprises the steps of providing a lid to close an infectious waste receptacle, and exposing the interior of the receptacle to a source of bactericidal light of sufficient intensity to kill the bacteria on the exposed surface of the accumulated waste in the receptacle and establish a substantially bacteria-free interface between the infectious waste and the surrounding environment. This surface bacteria is most likely to escape as the lid is opened or as additional waste is deposited in the receptacle. The method may also include the step of maintaining the interior of the receptacle at a lower pressure than the surrounding environment when the lid is closed, to retard the escape of contaminants such as bacteria. The method may also include the step of drawing air displaced from the receptacle away from a user when the lid is open. Finally, the method of the present invention may include the step of applying a disinfectant and/or deodorant to the accumulated waste in the receptacle to assist the bactericidal light source in establishing and maintaining the substantially bacteria-free interface between the infectious waste and the surrounding environment.

Generally, the device of the present invention comprises a frame and means on the frame for supporting and positioning an open-ended waste receptacle in the device. A lid is mounted on the frame to operate between a closed position in which the lid closes the open end of the receptacle and an open position in which the open end of the receptacle is exposed for the deposition of waste. A bactericidal light source is provided on the underside of the lid and is adapted to expose the interior of the receptacle to bactericidal light of sufficient intensity to kill the bacteria on the exposed surface of the accumulated waste in the receptacle and establish and maintain a substantially bacteria-free interface between the infectious waste and the surrounding environment. This surface bacteria is the most likely source of contamination as the lid is opened or as additional waste is deposited in the receptacle. The device may further be provided with a vent for maintaining the interior of the receptacle at a lower pressure than the surrounding environment when the lid is closed, to retard the escape of contaminants such as bacteria. The vent may also draw the potentially contaminated air displaced from the receptacle away from the user when the lid is open. Finally, the device may include means for applying a disinfectant and/or deodorant to the accumulated waste in the receptacle to supplement the bactericidal action of the light source and assist in establishing the substantially bacteria-free interface between the infectious waste and the surrounding environment.

In the preferred embodiment, the lid is hingedly mounted to the frame, preferably along the back edge of the lid, and the device includes means for remote, hands-free operation of the lid. It is also preferable that the vent be located adjacent to the back edge of the lid so that when the lid is open, air is drawn away from the front and sides of the receptacle where users might be. The bactericidal light source is preferably an ultraviolet light source, and the device preferably includes means for turning the light source off when the lid is open to protect persons in the surrounding environment from exposure to the ultraviolet light.

Generally, the receptacle of the present invention is of rectangular prismatic shape having a bottom, a front wall, a back wall, and two opposing sidewalls. The receptacle is sized to fit between two support arms on the device. Each sidewall has a side flap at its top edge. The side flaps are divided by a fold line into first portions adapted to extend over the tops of the support arms and second portions adapted to extend down over the exterior sides of the arms. The side flaps preferably extend beyond the back wall of the receptacle. The front wall has a front flap that is of greater length than the front to back dimension receptacle, to extend past the back wall when the front flap is folded over. The receptacle is preferably made of an inexpensive, light weight material such as cardboard, and thus is economically disposable. The receptacle is preferably constructed so that it can be collapsed or nested to be shipped and stored compactly. The receptacle is relatively rigid to prevent air from being expelled from the receptacle during handling.

The method and device of this invention thus inhibit contamination from infectious waste receptacles by providing a lid for enclosing the infectious waste, and a bacterial light source to kill bacteria on the exposed surface of the accumulated waste in the receptacle and establish a substantially bacteria-free interface between the infectious waste and the surrounding environment. It is thus surface bacteria that is most likely to escape as the lid is opened or as additional waste is deposited. The method and device provide a lid that is preferably remotely actuable to separate the user from the infectious waste as much as possible, and preferably can be operated hands-free to prevent cross-contamination of the users. A plenum and vent may be provided to retard the escape of bacteria by maintaining the interior of the receptacle at a lower pressure than the surrounding environment when the lid is closed. The vent and lid may be arranged so that the potentially contaminated air displaced from the receptacle is drawn away from the user. Finally, a disinfectant and/or deodorant may be applied to the accumulated waste in the receptacle to supplement the bactericidal light.

Other objects and features will be in part apparent and in part pointed out below.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
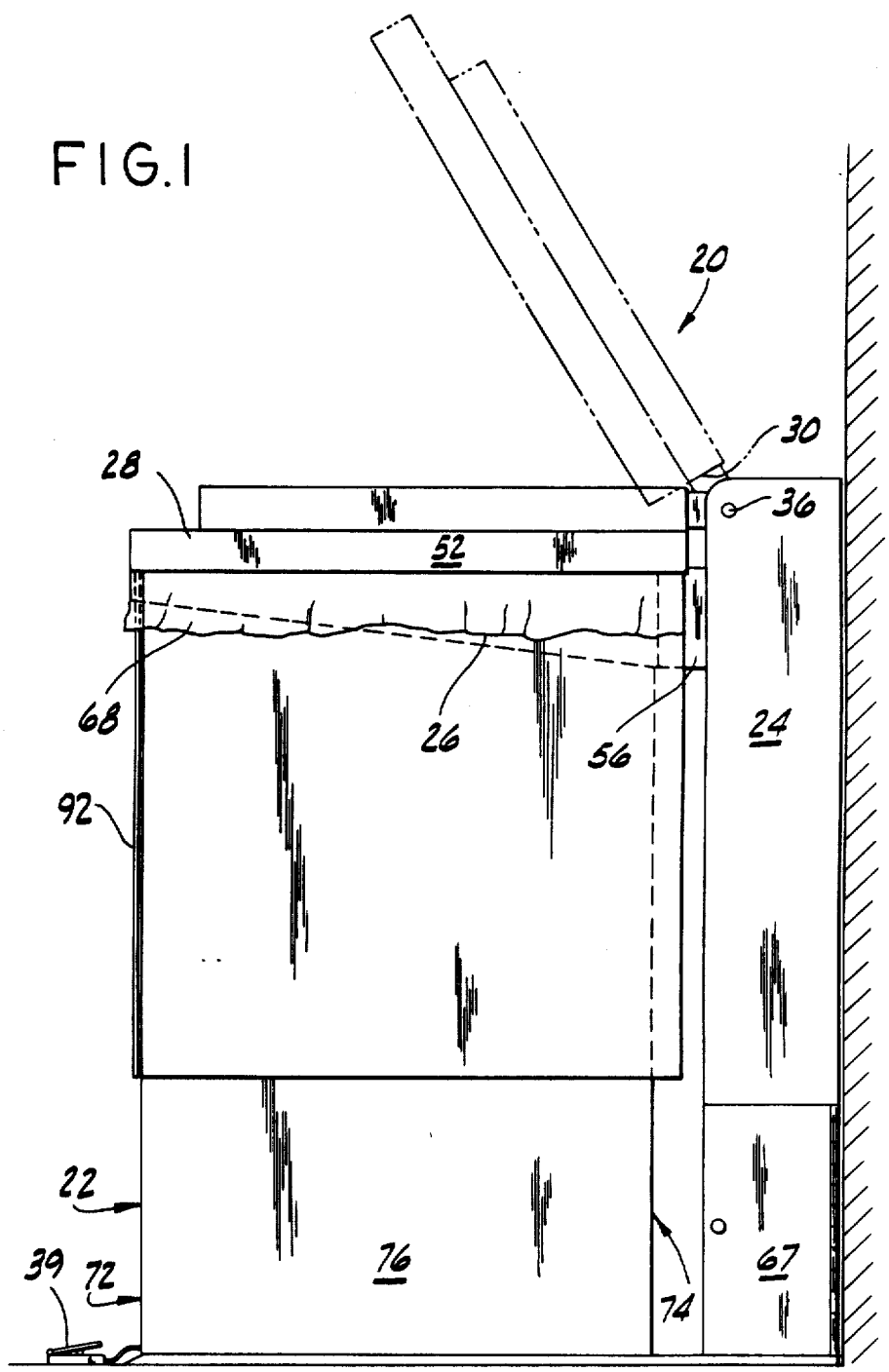
FIG. 1 is a right side elevation view of a device constructed according to the principles of this invention.
Figure 2:
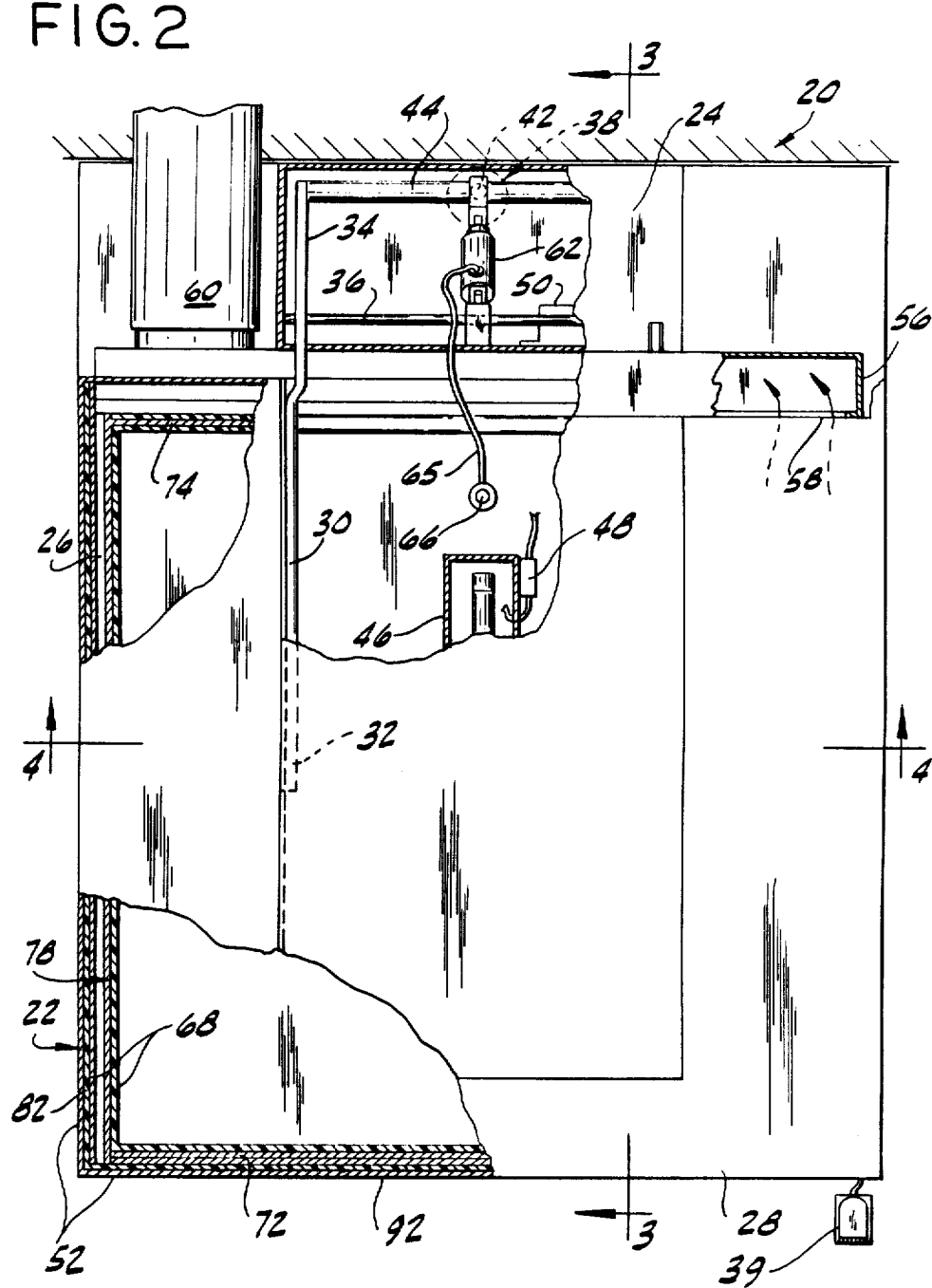
FIG. 2 is a top plan view of the device, with portions of the lid broken away.
Figure 3:
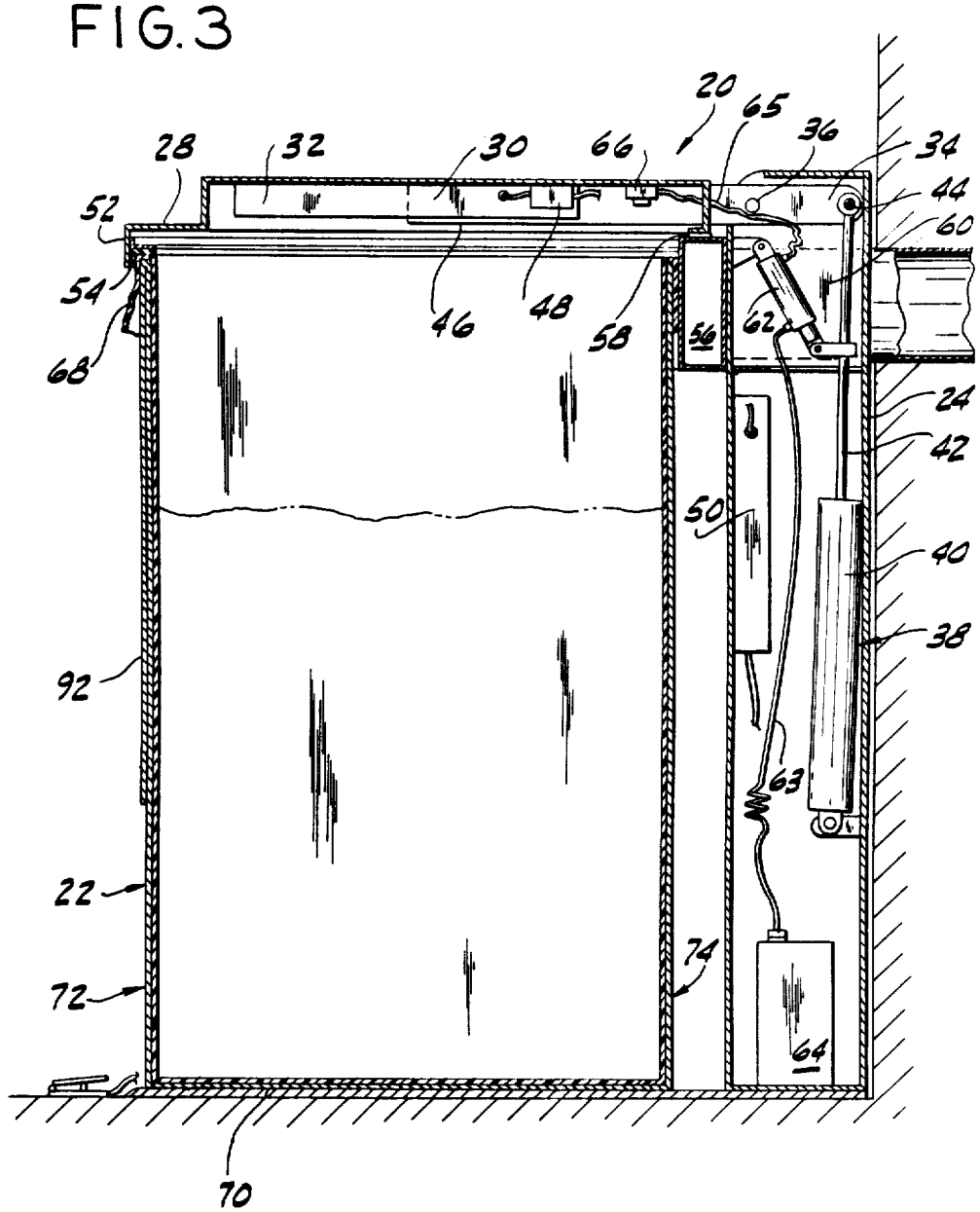
FIG. 3 is a cross sectional view of the device taken along the plane of line 3—3 in FIG. 2.
Figure 4:
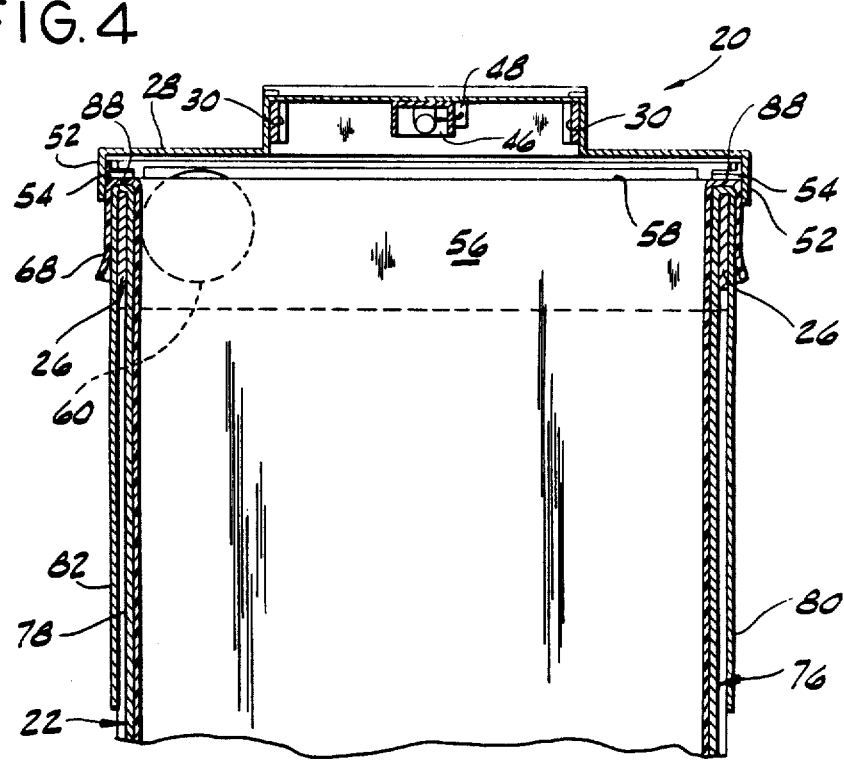
FIG. 4 is a partial cross sectional view of the device taken along the plane of line 4—4 in FIG. 2.

A device for inhibiting contamination from an infectious waste receptacle, constructed according to the principles of the present invention, is indicated generally as 20 in FIGS. 1-4. The device 20 is shown in the Figures with an open-ended receptacle 22 positioned therein for receipt of infectious waste.

The device 20 comprises a generally vertically extending hollow frame 24. Frame 24 may be mounted on a wall as shown in the Figures, or provided with wheels (not shown) so that the device is portable. Means, such as laterally-spaced, forwardly extending arms 26, are provided on the frame for supporting and positioning the receptacle 22 in the device. A lid 28 is mounted on the frame 24 in position to operate between a closed position in which the lid closes the open end of the receptacle 22 and an open position (shown in phantom in FIG. 1) in which the open end of the receptacle 22 is exposed for the deposition of waste.

In the preferred embodiment the lid 28 is pivotally mounted to the frame 24 at the lid's rearward edge. The lid 28 may be mounted by a pair of lid arms 30, each having a forward end 32 for supporting the lid 28 and a rearward end 34. A rod 36 pivotally mounts the lid arms 30 on the frame 24, intermediate their ends. Lid 28 can be remotely operated by solenoid 38 in frame 24. The core 40 of the solenoid 38 is attached to the frame 24, and the arm 42 of the solenoid is attached to a bar 44 extending between the rear ends 34 of the lid arms 30. The solenoid 38 can be remotely actuated by a pedal or switch 39 to selectively raise and lower the lid 28. Thus the user does not have to touch the lid 28 or even come in close contact with the opening in the infectious waste receptacle 22, thereby reducing the user's risk of contamination.

A light source 46 is mounted in a recess on the underside of the lid 28 in position to expose the interior of the receptacle to bactericidal light of sufficient intensity to kill bacteria on the exposed surface of the accumulated waste. The recess helps to protect light source 46 and provides a place for receiving the lid arms 30. The light establishes a substantially bacteria-free interface between the infectious waste and the surrounding environment. This surface bacteria is the most likely to escape from the receptacle when the lid is opened or as waste is deposited into the receptacle. The light source 46 is preferably an ultraviolet light source, and is preferably connected to a switch that automatically turns off the light when the lid is open, to protect persons around the device from the ultraviolet light. This switch may be a mercury position switch 48 that energizes the light source 46 only when the lid 28 is closed. Alternatively to or in addition to the mercury switch 48 a microswitch (not shown) can be located at the forward edge of the lid, to energize the light source 46 only when the microswitch contacts the receptacle 22. Of course, some other means, such as a shield, could be used to protect persons in the surrounding environment from exposure to the light. A ballast 50 for the light source 46 may be mounted in frame 24.

Lid 28 preferably has a depending peripheral lip 52 along the side and front edges to overlap the sides and front edges of the receptacle 22 when the lid is closed. A sealing gasket 54 can be provided on the underside of the lid 28 at the marginal edges to sealingly engage the top edges of the receptacle 22 to help prevent the escape of bacteria.

A plenum 56 may be positioned on frame 24 between the arms 26, and is adapted to abut the back of the receptacle. The plenum 56 has at least one vent 58 therein, positioned above the top edge of the receptacle but below the lid 28, and therefore communicates with the interior of the receptacle 22 when the lid 28 is closed. The vent 58 preferably comprises an elongate slot in the plenum 56 extending above the back of the receptacle 22 substantially the entire width of the receptacle. The plenum 56 may be connected, as with conduit 60, to a source of low pressure such as a ventilation duct. Such sources are frequently available in laboratories, hospitals, and other health care facilities. If a suitable source of low pressure is not already available, the plenum 56 could be connected to an exhaust fan (not shown). Such a fan could even be incorporated into the device along with a filter.

When the lid 28 is closed, vent 58 in plenum 56 maintains the interior of the receptacle 22 at a lower pressure than the surrounding environment to retard the escape of bacteria. In an embodiment of the device incorporating plenum 56, the lid 28 preferably does not form a perfect seal with the receptacle, so that air is continually drawn inwardly into the receptacle 22, through the vent 58 in the plenum 56, and out the conduit 60.

When the lid 28 is open, the vent 58 draws the potentially contaminated air displaced from the interior of the receptacle 22 rearwardly, away from any person who might be standing at the sides or front of the device. For this reason it is advantageous to position the plenum 56 and vent 58 adjacent the side where the lid 28 is hingedly mounted to the frame 24, so that air will always be drawn toward a protected side of the device and away from any users. The vent 58 is positioned to, and the air flow is sufficient to, establish an air curtain over the opening of the receptacle when the lid is open. This air curtain prevents any bacteria escaping from the receptacle and entering the surrounding environment.

The device 20 further comprises means for applying a disinfectant and/or deodorant to the waste in the receptacle 22 when the lid 28 opens, closes, or both. Such means may be, for example, spray pump 62 in frame 24, one portion of which may be attached to the frame 24 and the other portion of which may be secured to the arm 42 of the solenoid 38. Pump 62 is connected by tube 63 to a reservoir 64 of a disinfectant and/or deodorant. This disinfectant/deodorant will vary depending upon what substance has been approved by the appropriate regulatory authorities for the particular site. Movement of the arm 42 as the lid 28 pivots open causes pump 62 to draw disinfectant from reservoir 64 through tube 63. As the lid pivots closed, for example after additional infectious waste has been deposited, movement of the arm 42 causes pump 62 to pump the disinfectant though tube 65 to nozzle 66 where it is sprayed over the waste in the receptable, to kill bacteria on the exposed surface of the accumulated waste and assist light source 46 in establishing a substantially bacteria-free interface between the infectious waste and the surrounding environment. A hatch 67 can be provided in frame 24 so that the disinfectant reservoir can be replenished.

Figure 5:
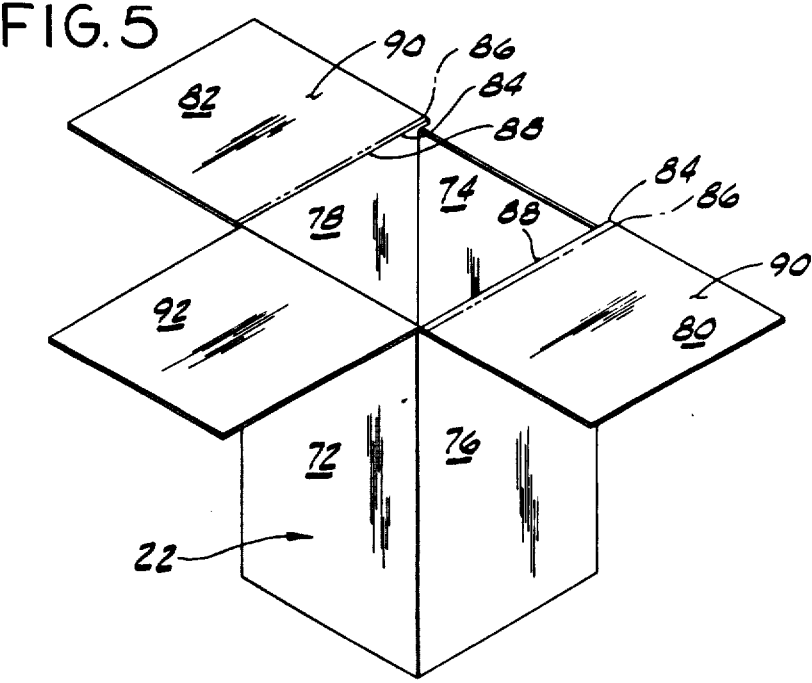
FIG. 5 is a perspective view of a receptacle constructed according to the principles of this invention, and particularly adapted for use with the device of this invention.

The receptacle 22 can be any type of waste receptacle, of any shape, but is preferably lined with a plastic bag liner 68. In the preferred embodiment, receptacle 22 is of generally rectangular prismatic shape comprising bottom 70, front wall 72, back wall 74, and opposing sidewalls 76 and 78. The receptacle is preferably made of a lightweight, inexpensive material such as cardboard, to be economically disposable. The receptacle is preferably constructed to be collapsable for easy handling during shipment and storage, yet can be easily assembled into a relatively rigid useable form. Rather than being made collapsable, receptacle 22 could be made nestable. The sidewalls 76 and 78 each have a side flap, 80 and 82, respectively, defined by a first fold line 84 at the top edge of the respective side wall. Each side flap also has a second fold line 86 closely spaced from the first fold line which separates each side flap into a relatively smaller first portion 88 adjacent the sidewall and adapted to extend over the top of one of the support arms 26, and a relatively larger second portion 90 adapted to extend over the exterior side of one of the support arms 26. As shown in FIG. 5, each of the side flaps 80 and 82 extends beyond the back wall 74 of the receptacle 22. The receptacle 22 preferably also includes a front flap 92 on the front wall adapted to be folded over the top of the receptacle 22 to close the receptacle. The front flap is formed by a fold 94 at the top edge of the front wall 72, and has a height greater than the front to back dimension of the receptacle 22 so that the front flap 92 extends beyond the back wall of the receptacle when the front flap 92 is folded over. The top edge of the back wall 74 is lower than the top edges of the front wall 72 and sidewalls 76 and 78, to accommodate the vent 58 in the plenum 56.

The receptacle 22 of the preferred embodiment is adapted for use with the device of the present invention, and is sized to fit between the forwardly extending arms 26. The first portions 88 of side flaps 80 and 82 are extended over the arms 26 and second portions 90 of the side flaps are folded downwardly at second fold lines 86 to extend downwardly over the outside of the arms. The lid 28 is sized to fit over the receptacle, the arms 26, and the flaps, and sandwich at least a portion of the side flaps 80 and 82 against the arms 26.

OPERATION

With the frame 24 mounted on the wall of, for example, a health care institution, and the plenum 56 connected to a suitable source of low pressure via conduit 60, the lid 28 is operated to its open position and a replaceable cardboard receptacle 22 is fit between the forwardly extending arms 26 of the device. The side flaps 80 and 82 are folded over the arm 26 by bending the flaps at fold lines 86 so that the first portions 88 of the flaps extend over the top of the arms 26 and the second portions 90 of the flaps extend downwardly over the sides of the arms 26. The lid 28 is then operated to the closed position, bringing the lid 28 down over the opening in receptacle with the lip 52 of the lid overlapping a portion of the front flap 92 and side flaps 80 and 82 and gasket 54 engages the top edges of the front and sides of the receptacle. The lid 28 sandwiches a portion of the side flaps 80 and 82 against arms 26.

When there is infectious waste to deposit in the receptacle 22, the lid 28 is operated to the open position. As the lid 28 opens, the mercury switch 48 deenergizes the light source 46 so that when the lid 28 is open persons around the device are not exposed to the bactericidal light. The waste is deposited into the receptacle. The air displaced by the infectious material deposited in the receptacle 22 is drawn by the vent 58 in the plenum 56 toward the back of the device away from the user standing at the front or sides of the device. After the waste is deposited into the receptacle 22, the lid 28 is operated closed. As the arm 42 of the solenoid 38 moves relative to the frame 24 as the lid 28 closes, pump 62 pumps disinfectant into the receptacle. When the lid is closed, mercury switch 48 again energizes the light source 46 which is of sufficient intensity to kill the bacteria on the exposed surface of the accumulated infectious waste and on the interior of the liner 68. This is the bacteria that is most likely to escape from the receptacle as the lid 28 is opened or as waste is deposited in the receptacle 22. The light establishes and maintains a substantially bacteria-free interface between the infectious waste and the surrounding environment. When the lid 28 is closed, the vent 58 in the plenum 56 maintains the interior of the receptacle 22 at a pressure below that in the surrounding environment so that air is drawn into the receptacle from the surrounding environment, through vent 58 in the plenum 56, and out conduit 60, thereby retarding the escape of bacteria to the surrounding environment.

When the receptacle 22 is full, the liner 68 can be closed. Any air inadvertently exhasted from the liner 68 during this process is drawn away from the worker by the vent 58 in the plenum 56. With the receptacle 22 still in place the side flaps 80 and 82 can be folded over one another over the opening in the receptacle 22 and the front flap 90 folded over the side flaps and secured to close the receptacle 22. The relatively rigid receptacle can then be removed. The receptacle protects the liner 68 during subsequent handling, preventing the liner 68 from being pierced or torn and prevents contaminated air from being squeezed from the liner 68.

There are various changes and modifications which may be made to this invention as would be apparent to one of ordinary skill in the art. However, any of these changes or modifications are included in the teaching of this disclosure and the inventor intends that this invention be limited only by the scope of the claims.

I claim:

1. A lid device for inhibiting contamination from an infectious waste receptacle, particularly while waste is being deposited therein, the device comprising:
    a frame;
    means on the frame for supporting and positioning an open-ended waste receptacle within the lid device;
    a lid;
    means for pivotally mounting the lid on the frame for pivotal movement between a closed position in which the lid closes the open end of a receptacle received in the supporting and positioning means and an open position in which the open end of the receptacle is exposed for deposition of waste, the means for mounting the lid comprising at least one lid arm having a forward end supporting the lid and a rearward end, and means for pivotally mounting the lid arm intermediate its ends to the frame;
    means for remotely pivoting the lid between its closed and open positions; the means for remotely pivoting the lid comprising a solenoid connected to the rearward end of the lid arm and means for remotely actuating the solenoid to move the lid arm to move the lid; and
    means for establishing a substantially bacteria-free interface between waste deposited in the receptacle and the surrounding environment.

2. The device according to claim 1 wherein the lid has an underside surface and the means for establishing a substantially bacteria-free interface comprises a bactericidal light source on the underside surface of the lid positioned so that when the lid is in its closed position the interior of a receptacle received in the supporting and positioning means is exposed to bactericidal light of sufficient intensity to kill bacteria on exposed surfaces of accumulated waste in the receptacle.

3. The device according to claim 2 wherein the bactericidal light source is a source of ultraviolet light.

4. The device according to claim 3 further comprising means for automatically turning off the bactericidal light source when the lid is moved from its closed position.

5. The device according to claim 1 wherein the lid is pivotally mounted to the frame at its rearward edge, and has a depending lip around the side and front edges for overlapping the sides and front of the receptacle.

6. A lid device for inhibiting contamination from an infectious waste receptacle, particularly while waste is being deposited therein, the device comprising:
    a frame;
    means on the frame for supporting and positioning an open-ended waste receptacle within the lid device;
    a lid;
    means for pivotally mounting the lid on the frame for pivotal movement between a closed position in which the lid closes the open end of a receptacle received in the supporting and positioning means and an open position in which the open end of the receptacle is exposed for deposition of waste; and
    means for establishing a substantially bacteria-free interface between waste deposited in the receptacle and the surrounding environment, the means for establishing the substantially bacteria-free interface comprising means for maintaining the interior of the receptacle at a lower pressure than the surrounding environment when the lid is closed to retard the escape of contaminants from the receptacle.

7. A lid device for inhibiting contamination from an infectious waste receptacle, particularly while waste is being deposited therein, the device comprising:
    a frame;

means on the frame for supporting and positioning an open-ended waste receptacle within the lid device;
a lid;
means for pivotally mounting the lid on the frame for pivotal movement between a closed position in which the lid closes the open end of a receptacle received in the supporting and positioning means and an open position in which the open end of the receptacle is exposed for deposition of waste; and
means for establishing a substantially bacteria-free interface between waste deposited in the receptacle and the surrounding environment, the means for establishing the substantially bacteria-free interface comprising means for drawing air over the open end of the receptacle when the lid is open to form an air curtain over the opening in the receptacle and inhibit the escape of contaminants from the receptacle.

8. A lid device for inhibiting contamination from an infectious waste receptacle, particularly while waste is being deposited therein, the device comprising:
a frame;
means on the frame for supporting and positioning an open-ended waste receptacle within the lid device;
a lid;
means for pivotally mounting the lid on the frame for pivotal movement between a closed position in which the lid closes the open end of a receptacle received in the supporting and positioning means and an open position in which the open end of the receptacle is exposed for deposition of waste; and
means for establishing a substantially bacteria-free interface between waste deposited in the receptacle and the surrounding environment, the means for establishing the substantially bacteria-free interface comprising a plenum on the frame adjacent the receptacle, the plenum having a vent above the top edge of the receptacle in communication with the interior of the receptacle, and means for connecting the plenum to a source of pressure lower than the environment surrounding the device to maintain the interior of the receptacle at a lower pressure than the surrounding environment when the lid is closed, to retard the escape of bacteria, and to draw the potentially contaminated air displaced from the receptacle by deposition of waste when the lid is open.

9. The device according to claim 8 wherein the lid is pivotally mounted to the frame adjacent a side of the receptacle and impairs access to that side of the receptacle, and wherein the vent in the plenum is positioned adjacent that side of the receptacle to draw potentially contaminated air displaced from the receptacle by deposition of waste away from the other sides of the receptacle where a depositor may be located.

10. A lid device for inhibiting contamination from an infectious waste receptacle, particularly while waste is being deposited therein, the device comprising:
a frame;
means on the frame for supporting and positioning an open-ended waste receptacle within the lid device, the means for supporting and positioning the receptacle comprising a pair of laterally spaced generally forwardly extending support members defining a space between them open in the front for receiving the receptacle, the open front permitting the installation and removal of the receptacle from the front of the device;
a lid;
means for pivotally mounting the lid on the frame for pivotal movement between a closed position in which the lid closes the open end of a receptacle received in the supporting and positioning means and an open position in which the open end of the receptacle is exposed for deposition of waste; and
means for establishing a substantially bacteria-free interface between waste deposited in the receptacle and the surrounding environment.

11. The device according to claim 10 wherein the means for establishing the substantially bacteria-free interface comprises a plenum on the frame between the support members and below the lid, the plenum adapted to abut a portion of the back of the receptacle and having at least one vent positioned above the top edge of the receptacle in communication with the interior, and means for connecting the plenum to a source of pressure lower than the environment surrounding the device to maintain the interior of the receptacle at a lower pressure than the surrounding environment when the lid is closed to retard the escape of bacteria, and to draw air displaced from the receptacle by the deposition of waste toward the back of the receptacle and away from a depositor of waste.

12. The device according to claim 10 wherein the device is adapted for use with a receptacle of generally rectangular prismatic shape, comprising a front wall, opposing side walls each having a hinged flap at the top edge, and a back wall, the support members extending forwardly from the frame and being sufficiently laterally spaced to receive the receptacle between them, with each support member extending between a side wall of the receptacle and its respective flap.

13. A lid device for inhibiting contamination from an infectious waste receptacle, particularly while waste is being deposited therein, the device comprising:
a frame;
two arms extending generally forwardly from the frame for supporting and positioning an open-ended waste receptacle within the lid device;
a lid, having an underside surface;
means for pivotally mounting the lid on the frame, adjacent the back of a receptacle received between the arms for pivoting between a closed position in which the lid closes the open end of the receptacle and an open position in which the open end of the receptacle is exposed for deposition of waste, the lid impairing access to at least a portion of the back of the receptacle;
a bactericidal light source on the underside of the lid positioned to expose the interior of the receptacle to bactericidal light of sufficient intensity to kill bacteria on exposed surfaces of accumulated waste in the receptacle and establish a substantially bacteria-free interface between the accumulated waste and the surrounding environment;
a plenum on the frame adjacent the back of the receptacle, the plenum having a vent above the top edge of the back of the receptacle in communication with the interior of the receptacle; and
means for connecting the plenum to a source of pressure lower than the surrounding environment to maintain the interior of the receptacle at a lower pressure than the surrounding environment when the lid is closed to retard the escape of contaminants, and to draw the potentially contaminated air displaced from the receptacle by deposition of waste toward the back of the receptacle and away from the other sides of the receptacle where a depositor may be located.

14. The device according to claim 13 further comprising means for automatically applying a disinfectant to exposed surfaces of accumulated waste in the receptacle when the lid is pivoted between its closed and open positions.

15. A lid device and infectious waste receptacle combination for inhibiting contamination from infectious waste, particularly while waste is being deposited in the receptacle, the combination comprising:
   a receptacle comprising: a front wall, opposing sidewalls each having a hinged side flap at the top edge, and a back wall, the walls defining an open top,
   a lid device comprising:
   a frame;
   two support members extending forwardly from the frame, the support members laterally spaced to receive the receptacle between them with each support member extending between a side of the receptacle and its respective flap;
   a lid
   means for pivotally mounting the lid on the frame for movement between a closed position in which the lid closes the open end of the receptacle and an open position in which the open end of the receptacle is exposed for the deposition of waste, the lid substantially impairing access to the back of the receptacle, the lid having a depending peripheral lip along the side and front edges of the lid to overlap the sides and front of the receptacle when the lid is in its closed position;
   means for establishing a substantially bacteria-free interface between the infectious waste deposited in the receptacle and the surrounding environment, the means for establishing the substantially bacteria-free interface comprising a plenum on the frame between the support members and below the lid, the plenum adapted to abut the back wall of the receptacle received between the arms, the plenum having at least one vent positioned above the top edge of the back wall of the receptacle in communication with the interior of the receptacle;
   means for connecting the plenum to a source of pressure lower than the surrounding environment to maintain the interior of the receptacle at a lower pressure than the surrounding environment when the lid is closed, to retard the escape of bacteria, and to draw the potentially contaminated air displaced from the receptacle by the deposition of waste toward the back of the receptacle and away from the other sides of the receptacle where the depositor may be located.

16. The combination according to claim 15 wherein the top edge of the back wall of the receptacle is lower than the top edges of the front wall and sidewalls.

17. The combination according to claim 15 wherein the means for establishing the bacteria-free interface comprises means for automatically applying a disinfectant to the exposed surface of the accumulated waste in the receptacle.

18. The combination according to claim 15 wherein each side flap further comprises a fold line separating the flap into a relatively smaller first portion adapted to extend over the top of the support member on the device, and a relatively larger second portion adapted to extend downwardly over the exterior side of the support member and wherein the support members and the lid are relatively positioned to sandwich a portion of the side flaps between them.

19. The combination according to claim 18 wherein the receptacle further comprises a front flap on the front wall adapted to be folded over the top of the receptacle, the flap being longer than the front to back dimension of the receptacle to extend beyond the back wall of the receptacle when folded over.

20. A receptacle for use with a lid device having a frame and two forwardly extending laterally spaced support arms extending from the frame for receiving and supporting the receptacle and a pivotally mounted lid for closing the receptacle, the receptacle comprising:
   a bottom;
   a front wall;
   a back wall;
   and two opposing sidewalls, each side having a side flap defined by a first fold line at the top edge of the sidewall, each side flap having a second fold line closely spaced to the first fold line and separating the side flap into a relatively smaller first portion adjacent the sidewall adapted to extend over the top of a support arm, and a relatively larger second portion adapted to extend over the exterior side of the support arm, each side flap extending rearwardly beyond the back wall of the receptacle.

21. The receptacle according to claim 20 wherein the receptacle further comprising a front flap on the front wall adapted to be folded over the top of the receptacle, the front flap having a length greater than the front to back dimension of the receptacle so that it extends beyond the back wall of the receptacle when it is folded over.

22. A lid device for inhibiting contamination from an infectious waste receptacle, particularly while waste is is being deposited therein, the device comprising:
   a frame;
   means on the frame for supporting and positioning an open-ended waste receptacle within the lid device;
   a lid;
   means for mounting the lid on the frame for movement between a closed position in which the lid closes the open end of a receptacle received in the supporting and positioning means, and an open position in which the open end of the receptacle is exposed for deposition of waste; and
   means for maintaining the interior of the receptacle at a lower pressure than the surrounding environment when the lid is in its closed position to retard escape of contaminants from waste in the receptacle, including means for connecting the interior of the receptacle to a source of pressure lower than the surrounding atmosphere.

23. The device according to claim 22 wherein the lid has an underside surface and further comprising a bactericidal light source on the underside of the lid positioned so that when the lid is in its closed position the interior of a receptacle received in the supporting and positioning means is exposed to bactericidal light of sufficient intensity to kill bacteria on exposed surfaces of accumulated waste in the receptacle and establish a substantially bacteria-free interface between the waste and the surrounding environment.

24. A lid device for inhibiting contamination from an infectious waste receptacle, particularly while waste is is being deposited therein, the device comprising:

a frame;

means on the frame for supporting and positioning an open-ended waste receptacle within the lid device;

a lid;

means for mounting the lid on the frame for movement between a closed position in which the lid closes the open end of a receptacle received in the supporting and positioning means, and an open position in which the open end of the receptacle is exposed for deposition of waste; and means for drawing air over the open end of the receptacle when the lid is in its open position to form an air curtain over the opening of the receptacle and inhibit the escape of contaminants from the receptacle.

25. The device according to claim 35 wherein the lid has an underside surface and further comprising a bactericidal light source on the underside of the lid positioned so that when the lid is in its closed position the interior of a receptacle received in the supporting and positioning means is exposed to bactericidal light of sufficient intensity to kill bacteria on exposed surfaces of accumulated infectious waste in the receptacle and establish a substantially bacteria-free interface between the infectious waste and the surrounding environment.

26. A lid device for inhibiting contamination from an infectious waste receptacle, particularly while waste is is being deposited therein, the device comprising:

a frame;

means on the frame for supporting and positioning an open-ended waste receptacle within the lid device;

a lid;

means for mounting the lid on the frame for movement between a closed position in which the lid closes the open end of a receptacle received in the supporting and positioning means, and an open position in which the open end of the receptacle is exposed for deposition of waste; and a plenum on the frame adjacent a receptacle received in the supporting and positioning means, the plenum having a vent above the top edge of the receptacle in communication with the interior of the receptacle, and means for connecting the plenum to a source of pressure lower than the environment surrounding the receptacle to maintain the interior of the receptacle at a lower pressure than the surrounding environment when the lid is in its closed position to retard escape of contaminants, and to draw the potentially contaminated air displaced from the receptacle by deposition of waste when the lid is in its open position.

27. The device according to claim 26 wherein the lid is pivotally mounted to the frame adjacent a side of the receptacle received in the supporting and positioning means and thereby impairs access to that side of the receptacle, and wherein the vent in the plenum is positioned adjacent that side of the receptacle to draw potentially contaminated air displaced from the receptacle by deposition of waste away from the other sides of the receptacle where a despositor may be located.

28. The device according to claim 26 wherein the lid has an underside surface and further comprising a bactericidal light source on the underside of the lid positioned so that when the lid is in its closed position the interior of a receptacle received in the supporting and positioning means is exposed to bactericidal light of sufficient intensity to kill bacteria on exposed surfaces of accumulated infectious waste in the receptacle and establish a substantially bacteria-free interface between the infectious waste and the surrounding environment.

* * * * *

UNITED STATES PATENT AND TRADEMARK OFFICE
CERTIFICATE OF CORRECTION

PATENT NO. : 4,902,482
DATED : February 20, 1990
INVENTOR(S) : Paul A. Faust

It is certified that error appears in the above-identified patent and that said Letters Patent is hereby corrected as shown below:

In the title of the cover page, "Infections", should read ---Infectious---.

Column 12, line 19, "side having", should read ---side wall having---.

Column 12, line 30, "comprising", should read ---comprises---.

Signed and Sealed this

Fourth Day of June, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,902,482
DATED : February 20, 1990
INVENTOR(S) : Paul A. Faust It is certified that error appears in the above-identified patent and that said Letters Patent is hereby corrected as shown below:

Column 13, claim 25, line 16, "claim 35" should read ---claim 24---.

Signed and Sealed this

Twenty-fourth Day of August, 1993

Attest:

*Attesting Officer*

BRUCE LEHMAN

*Commissioner of Patents and Trademarks*